United States Patent
Deshays

(10) Patent No.: US 8,623,275 B2
(45) Date of Patent: Jan. 7, 2014

(54) MEDICAL INSTRUMENT DISINFECTING SYSTEM

(75) Inventor: Clement Deshays, Ruoms (FR)

(73) Assignee: Germitec, Clichy (FR)

( * ) Notice: Subject to any disclaimer, the term of this patent is extended or adjusted under 35 U.S.C. 154(b) by 255 days.

(21) Appl. No.: 12/296,571

(22) PCT Filed: Apr. 6, 2007

(86) PCT No.: PCT/FR2007/000594
§ 371 (c)(1),
(2), (4) Date: Oct. 9, 2008

(87) PCT Pub. No.: WO2007/116142
PCT Pub. Date: Oct. 18, 2007

(65) Prior Publication Data
US 2009/0169436 A1   Jul. 2, 2009

(30) Foreign Application Priority Data
Apr. 10, 2006  (FR) ...................... 06 03168

(51) Int. Cl.
*A61L 2/00* (2006.01)
*A61B 1/00* (2006.01)
*G01N 23/00* (2006.01)

(52) U.S. Cl.
USPC .......... 422/24; 422/1; 422/3; 422/62; 422/28; 600/133; 250/455.11

(58) Field of Classification Search
USPC ........... 422/1, 3, 24, 62, 28; 134/22.1, 166 R, 134/198, 56 R; 600/133; 250/455.11
See application file for complete search history.

(56) References Cited

U.S. PATENT DOCUMENTS

| | | | |
|---|---|---|---|
| 4,772,795 A | 9/1988 | Sakurai et al. | |
| 4,948,566 A | 8/1990 | Gabele et al. | |
| 5,185,532 A | 2/1993 | Zabsky et al. | |
| 5,310,524 A | 5/1994 | Campbell et al. | |

(Continued)

FOREIGN PATENT DOCUMENTS

| | | |
|---|---|---|
| DE | 3209701 A1 | 9/1983 |
| DE | 3917876 A1 | 12/1990 |

(Continued)

OTHER PUBLICATIONS

International Search Report of PCT/FR2005/003032, date for mailing Jul. 6, 2006, ISR of co-pending U.S. Appl. No. 12/066,872.

(Continued)

*Primary Examiner* — Monzer Chorbaji
(74) *Attorney, Agent, or Firm* — Morrison & Foerster LLP

(57) ABSTRACT

This disinfection system for medical instruments of the type comprising a disinfection chamber adapted to implement a cycle for disinfecting instruments, is characterized in that each instrument is associated with a radiofrequency label containing identification information and in that the chamber is associated with radiofrequency means for acquiring identification information about the or each instrument when put in place and removed from the chamber at the start and end of a disinfection cycle, with means of acquiring information characterizing the disinfection cycle and with means for combining identification information about the or each instrument with information characterizing the disinfection cycle in order to generate traceability information on the disinfection of the or each instrument.

2 Claims, 1 Drawing Sheet

(56) References Cited

U.S. PATENT DOCUMENTS

| | | |
|---|---|---|
| 5,610,811 A | 3/1997 | Honda |
| 5,641,464 A | 6/1997 | Briggs, III et al. |
| 5,690,113 A | 11/1997 | Sliwa, Jr. et al. |
| 5,761,069 A | 6/1998 | Weber et al. |
| 5,912,818 A | 6/1999 | McGrady et al. |
| 6,039,928 A | 3/2000 | Roberts |
| 6,171,559 B1 | 1/2001 | Sanders et al. |
| 6,231,819 B1 | 5/2001 | Morello |
| 6,260,560 B1 | 7/2001 | Walta |
| 6,371,326 B1 | 4/2002 | Gabele et al. |
| 6,475,433 B2 | 11/2002 | McGeorge et al. |
| 6,485,979 B1 | 11/2002 | Kippenhan et al. |
| 6,641,781 B2 | 11/2003 | Walta |
| 6,712,756 B1 | 3/2004 | Kura et al. |
| 7,694,814 B1 | 4/2010 | Cristobal et al. |
| 7,965,185 B2 | 6/2011 | Cambre et al. |
| 7,982,199 B2 | 7/2011 | Deshays |
| 8,313,017 B2 | 11/2012 | Deshays |
| 8,334,521 B2 | 12/2012 | Deshays |
| 8,356,745 B2 | 1/2013 | Deshays |
| 2001/0024623 A1 | 9/2001 | Grimm et al. |
| 2002/0161460 A1 | 10/2002 | Noguchi |
| 2002/0162972 A1 | 11/2002 | Pleet |
| 2003/0016122 A1 | 1/2003 | Petrick |
| 2003/0039579 A1 | 2/2003 | Lambert et al. |
| 2003/0091471 A1 | 5/2003 | Lacabanne |
| 2003/0187586 A1 | 10/2003 | Katzenmaier et al. |
| 2004/0009091 A1* | 1/2004 | Deal et al. ............ 422/3 |
| 2004/0140347 A1 | 7/2004 | Mihaylov et al. |
| 2004/0209223 A1 | 10/2004 | Beier et al. |
| 2005/0196314 A1* | 9/2005 | Petersen et al. ............ 422/3 |
| 2007/0027459 A1 | 2/2007 | Horvath et al. |
| 2008/0213139 A1 | 9/2008 | Deshays |
| 2008/0219899 A1 | 9/2008 | Deshays |
| 2009/0065034 A1 | 3/2009 | Suzuki et al. |
| 2010/0138234 A1 | 6/2010 | Deshays |
| 2010/0140134 A1 | 6/2010 | Deshays |
| 2010/0140342 A1 | 6/2010 | Deshays |
| 2010/0145721 A1 | 6/2010 | Deshays |

FOREIGN PATENT DOCUMENTS

| | | |
|---|---|---|
| DE | 44 20 707 A1 | 12/1994 |
| DE | 195 14 284 A1 | 10/1996 |
| DE | 197 03 823 C1 | 5/1998 |
| DE | 199 17 206 A1 | 10/2000 |
| DE | 102 25 232 A1 | 12/2002 |
| DE | 102 25 857 A1 | 1/2004 |
| EP | 0471530 A | 2/1992 |
| EP | 0630820 A | 12/1994 |
| EP | 0709056 A1 | 5/1996 |
| EP | 0 839 537 A1 | 5/1998 |
| EP | 1 155 654 A1 | 11/2001 |
| EP | 1402904 A | 3/2004 |
| EP | 1 532 989 A1 | 5/2005 |
| FR | 2753905 A1 | 4/1998 |
| FR | 2 890 864 A1 | 3/2007 |
| FR | 2890566 A1 | 3/2007 |
| FR | 2890865 A1 | 3/2007 |
| WO | WO-84/00009 A1 | 1/1984 |
| WO | WO-99/08137 A1 | 2/1999 |
| WO | WO-99/66444 A1 | 12/1999 |
| WO | WO-01/80908 A1 | 11/2001 |
| WO | 2004/111917 A1 | 12/2004 |
| WO | WO-2005/048041 A2 | 5/2005 |
| WO | WO-2005/048041 A3 | 5/2005 |
| WO | WO-2006/115177 A1 | 11/2006 |
| WO | WO-2007/016101 A1 | 2/2007 |
| WO | WO-2007/034083 A1 | 3/2007 |

OTHER PUBLICATIONS

International Search Report mailed on Mar. 21, 2006 for PCT Application No. PCT/FR2005/003031, 3 pages.

International Search Report mailed on Jan. 22, 2009 for PCT Application No. PCT/FR2008/000540, 3 pages.

International Search Report mailed on Jan. 22, 2009, for PCT Application No. PCT/FR2008/000541, 3 pages.

International Search Report mailed on Feb. 23, 2009 for PCT Application No. PCT/FR2008/000465, filed on Apr. 3, 2008, 3 pages.

International Search Report mailed on Feb. 23, 2009 for PCT Application No. PCT/FR2008/000464, filed on Apr. 3, 2008, 3 pages.

International Search Report mailed on Jul. 18, 2006, for PCT Application No. PCT/FR2005/003034, 3 pages.

International Search Report of PCT/FR2007/000594, date of mailing Sep. 11, 2007.

* cited by examiner

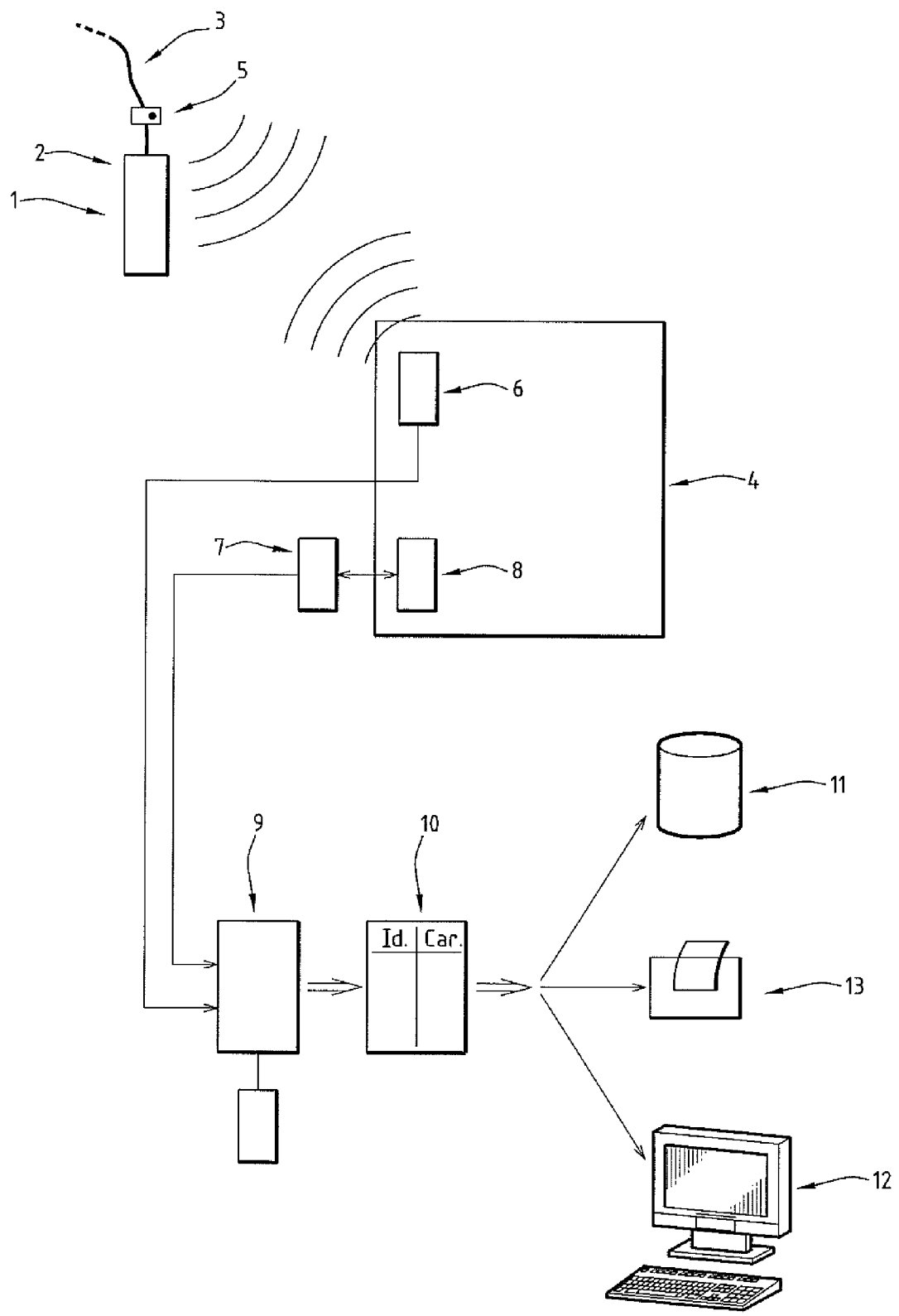

MEDICAL INSTRUMENT DISINFECTING SYSTEM

This invention concerns a system for disinfecting medical instruments.

In the state-of-the-art we are already aware of disinfecting systems of this type which comprise for example a disinfection chamber adapted to implement an instrument disinfection cycle.

These chambers can for example be chambers combined with means of emitting type UVC UV radiation for example or with means of chemical disinfection, etc.

As an example, reference can be made to document EP-A-0839537 which describes a device for holding instruments in a chamber in particular a decontamination chamber and a corresponding chamber.

In fact this document refers to a decontamination chamber for medical instruments delimited by a base, at least one side wall and an upper cover, with each instrument having an active part and a connection part in the form of a cable.

This chamber also has a bracket extending into the interior and into the upper part of the chamber, in parallel with the base and overhanging the base, with this bracket comprising numerous suspension elements, each of these being intended to cooperate with part of the neighbouring cable from the active part of the instrument.

This chamber is also combined with means for example with tubes emitting type C UV radiation into the latter for example in order to ensure disinfecting of the instruments.

Obviously, other means of disinfecting can be envisaged.

However, all the systems in the state-of-the-art pose a number of problems in particular with regard to the traceability of instrument disinfection.

The purpose of the invention is therefore to resolve these problems.

To this end, the subject of the invention is a disinfection chamber adapted to implement an instrument disinfection cycle, characterised in that each instrument is combined with a radiofrequency label containing identification information and in that the chamber is combined with radiofrequency means of acquiring identification information about the or each instrument when put in place and removed from the chamber at the start and end of a disinfection cycle, with means of acquiring information characterising the disinfection cycle and with means of combining identification information about the or each instrument with information characterising the disinfection cycle in order to generate traceability information about the disinfection of the or each instrument.

According to the particular methods of construction, the chamber in accordance with the invention has one or several of the following characteristics:
the chamber has a bracket for suspending instruments;
the means of acquiring information characterising the disinfection cycle comprise means of acquiring information selected from the group of information containing information identifying the chamber and information relating to the date and time of the disinfection cycle;
the chamber has means for generating UV radiation for disinfecting the instruments and the information characterising the disinfection cycle comprises information on the dose of UV issued during the cycle, from a corresponding sensor located in the chamber;
the UV sensor is located under the chamber bracket;
the means of combining information are combined with means for displaying, storing and/or printing this information;
the means of combining information are adapted so as to issue information on traceability only if the corresponding instrument was clearly identified when put in place and removed from the chamber before and after the disinfection cycle, respectively.

The invention will be better understood using the following description, provided solely as an example and produced with reference to the attached drawing which represents a block diagram illustrating the structure and functioning of a disinfection system according to the invention.

In fact this FIGURE illustrates a system for disinfecting medical instruments.

An instrument of this type is for example designated by the general reference 1 on this FIGURE and is presented for example in the form of a probe of an echographic probe type or other.

This probe then has an active part designated by the general reference 2 and a connection cable designated by the general reference 3.

This probe is adapted to be put in place and removed from a disinfection chamber designated by the general reference 4 on the FIGURE. This disinfection chamber is adapted to implement an instrument disinfection cycle.

As mentioned previously, various types of chamber and various types of disinfection cycles can be envisaged whether this involves for example radiation, chemical or other disinfection.

In the system according to the invention, each instrument carries information identifying it.

This identification information can be stored in an electronic radiofrequency label designated by the general reference 5 on the FIGURE, with this label being for example carried by the active part or even by the instrument connection cable.

Obviously, other methods of construction can be envisaged.

The chamber is then combined with radiofrequency means for acquiring this identification information for each instrument.

These means of acquiring this identification information are designated by the general reference 6 on this FIGURE and comprise for example any appropriate sensor of a traditional type, placed for example in the chamber.

This sensor is then adapted to acquire identification information about the or each instrument when placed in and removed from the chamber at the start and end of a disinfection cycle.

As an example, these means of acquisition can be presented in the form of a sensor directly integrated in the disinfection chamber for example on the bracket of the chamber described in document EP-A-0839537 referred to previously or even in the latter's side walls.

In addition, the chamber is combined with means of acquiring information characterising the decontamination cycle, namely more specifically the conditions of its progress.

These means are designated by the general reference 7 on this FIGURE and can consist of various types of means of acquiring information adapted to acquire information selected from a group of information comprising for example information identifying the chamber, with each chamber then being allocated a specific identification number stored in the latter, with information on dating the cycle for example allowing acquisition of the date of the cycle, the daily number of the cycle, the start time and end time of the cycle, from a circuit forming a clock, etc.

This characterisation information can also contain information relating to the dose of UV emitted during a cycle if the chamber is a disinfecting chamber equipped with means for generating disinfecting UV radiation.

This information can then be determined from a sensor of any appropriate type already known in the state-of-the-art and designated for example by the general reference 8 on this FIGURE.

This sensor can then be located for example under the bracket of the chamber described in the EP document referred to previously.

This various information, namely the information identifying the or each instrument and the information characterising the disinfection cycle, is then transmitted to a unit for processing information designated by the general reference 9 on this FIGURE and constituted by any appropriate calculator, for example integrated in the means for regulating the chamber operations, in order to implement a function for combining this information in order to generate disinfecting traceability information.

In fact, this information processing unit 9 is adapted to combine the identification information of the or each instrument present in the chamber during a disinfection cycle with the information characterising the progress of this cycle, in order to issue the information capable of guaranteeing the disinfecting traceability of the or each instrument.

This traceability information is designated by the general reference 10 on the FIGURE and therefore allows each instrument to be brought into relation with the conditions under which the corresponding disinfection cycle takes place.

It should be pointed out that this traceability information can only be issued if an instrument has been clearly identified at the time of its introduction into the chamber prior to the start of the cycle and when it is removed from this chamber after the end of this cycle.

It is therefore essential for the operator to identify the instrument when it is put in place and removed from the chamber. If this is not the case, the information processing unit does not generate the traceability information.

This traceability information is then available to ensure the traceability of the disinfection operation with a view for example to storing this information in information storage means as illustrated in 11 on this FIGURE, to displaying this for example on any display designated by the general reference 12, or even by a print-out of this information for example using any printing means such as a printer designated by the general reference 13.

It can be seen for example that a printer of this type can be adapted to print traceability information on a sticker which can be associated for example with a file on the patient who has been in contact with the disinfected instrument, a traceability register, etc.

As an example, the characterisation information carried by this sticker then contains information about the UV dose received by the instrument when it moves into the disinfecting chamber, with this dose being for example determined from the UV power or irradiation issued during the cycle multiplied by the duration of this cycle.

We know in fact that this parameter can be a determining factor for obtaining this or that level of instrument disinfection.

We then believe that a system of this type is able to ensure optimum traceability for disinfecting instruments of this type insofar as the traceability information is able to guarantee that the instrument has passed into the chamber and to check the information on the characterisation of the disinfection cycle to which the instrument has been submitted, namely in particular the point when this disinfection took place, the chamber in which the disinfection cycle took place and in particular the dose of UV received by the instrument.

Obviously, other methods of construction can still be envisaged.

The invention claimed is:

1. Method of disinfecting medical instruments in a disinfection chamber configured to implement an instrument disinfection cycle for disinfecting at least one instrument among a group of instruments and comprising a cable connection, wherein each instrument of the group has an active part and a cable, and is associated with a respective radiofrequency label on the cable connection containing respective identification information identifying said instrument among other instruments of the group, said method comprising:
   suspending the at least one instrument from a suspension bracket; wherein the chamber comprises a sensor, the sensor being integrated to the suspension bracket
   using a radiofrequency reader to acquire the respective identification information of each instrument subjected to the disinfection cycle,
   disinfecting the at least one instrument by emitting radiation from a UV radiation source,
   using the sensor of the disinfection chamber to acquire information characterising the disinfection cycle, and
   processing the identification and characterizing information by combining the respective identification information of each instrument subjected to the disinfection cycle and the information characterising the disinfection cycle in order to generate traceability information on the disinfection of each instrument subjected to the disinfection cycle in the disinfection chamber.

2. Disinfecting method according to claim 1, wherein the identification information is acquired (i) at a first time during a first time period from an introduction of said at least one instrument into the chamber to a start of the disinfection cycle, and (ii) at a second time during a second time period from an end of the disinfection cycle to a removal of said at least one instrument from the chamber.

* * * * *